US00PP36277P2

(12) United States Plant Patent
Mousa

(10) Patent No.: US PP36,277 P2
(45) Date of Patent: Nov. 26, 2024

(54) ***CUPHEA* PLANT NAMED 'Docupla 24'**

(50) Latin Name: *Cuphea hyssopifolia*
Varietal Denomination: Docupla 24

(71) Applicant: DUMMEN GROUP B.V., De Lier (NL)

(72) Inventor: Rami Mousa, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/581,252

(22) Filed: Feb. 19, 2024

(51) Int. Cl.
*A01H 6/00* (2018.01)
*A01H 5/02* (2018.01)

(52) U.S. Cl.
USPC ..... Plt./420

(58) Field of Classification Search
USPC ..... Plt./420
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Cuphea* plant named 'Docupla 24', characterized by its compact and semi-upright growth habit; moderately vigorous and moderate growth rate; freely branching habit; early and freely flowering habit; purplish red-colored flowers; and good garden performance and relative tolerance to high temperatures.

1 Drawing Sheet

Botanical designation: *Cuphea hyssopifolia.*
Cultivar denomination: 'DOCUPLA 24'.

STATEMENT REGARDING PRIOR DISCLOSURES BY INVENTOR AND APPLICANT/ASSIGNEE

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Cuphea* plant, botanically known as *Cuphea hyssopifolia* and hereinafter referred to by the name 'Docupla 24'.

The new *Cuphea* plant is a product of a planned breeding program conducted by the Inventor in De Lier, The Netherlands. The objective of the breeding program is to create new freely branching *Cuphea* plants with numerous attractive flowers and good garden performance.

The new *Cuphea* plant originated from a cross-pollination during the autumn of 2018 in De Lier, The Netherlands of a proprietary selection of *Cuphea hyssopifolia* identified as code number CU-0010, not patented, as the female, or seed, parent with a proprietary selection of *Cuphea hyssopifolia* identified as code number CU-0021, not patented, as the male, or pollen, parent. The new *Cuphea* plant was discovered and selected by the Inventor as a single flowering plant within the progeny of the stated cross-pollination in a controlled greenhouse environment in De Lier, The Netherlands during the summer of 2019.

Asexual reproduction of the new *Cuphea* plant by cuttings in a controlled greenhouse environment in De Lier, The Netherlands since the autumn of 2019, has shown that the unique features of this new *Cuphea* plant are stable and reproduced true to type in successive generations.

SUMMARY OF THE INVENTION

Plants of the new *Cuphea* have not been observed under all possible combinations of environmental conditions and cultural practices. The phenotype may vary somewhat with variations in environment and cultural practices such as temperature and light intensity without, however, any variance in genotype.

The following traits have been repeatedly observed and are determined to be the unique characteristics of 'Docupla 24'. These characteristics in combination distinguish 'Docupla 24' as a new and distinct cultivar of *Cuphea* plant:

1. Compact and semi-upright growth habit.
2. Moderately vigorous and moderate growth rate.
3. Freely branching habit.
4. Early and freely flowering habit.
5. Purplish red-colored flowers.
6. Good garden performance and relatively tolerant to high temperatures.

Plants of the new *Cuphea* can be compared to plants of the female parent selection. Plants of the new *Cuphea* differ primarily from plants of the female parent selection in flower color as plants of the new *Cuphea* have purplish red-colored flowers whereas plants of the female parent selection have light magenta-colored flowers.

Plants of the new *Cuphea* can be compared to plants of the male parent selection. Plants of the new *Cuphea* differ primarily from plants of the male parent selection in flower color as plants of the new *Cuphea* have purplish red-colored flowers whereas plants of the male parent selection have pink-colored flowers. In addition, plants of the new *Cuphea* flower earlier than plants of the male parent selection.

Plants of the new *Cuphea* can also be compared to plants of the *Cuphea hyssopifolia 'Cuphea* Lilac', not patented. In side-by-side comparisons conducted in De Lier, The Netherlands, plants of the new *Cuphea* differ primarily from plants of '*Cuphea* Lilac' in flower color as plants of the new *Cuphea* have purplish red-colored flowers whereas plants of '*Cuphea* Lilac' have lighter purplish red to purplish pink-colored flowers.

BRIEF DESCRIPTION OF THE PHOTOGRAPH

The accompanying colored photograph illustrates the overall appearance of the new *Cuphea* plant showing the colors as true as it is reasonably possible to obtain in colored reproductions of this type. Colors in the photograph may differ slightly from the color values cited in the detailed botanical description which accurately describe the colors of the new *Cuphea* plant.

The photograph is a side perspective view of a typical flowering plant of 'Docupla 24' grown in a container.

DETAILED BOTANICAL DESCRIPTION

The aforementioned photograph and following observations, measurements and values describe plants grown during the summer in 12-cm containers in a glass-covered greenhouse in De Lier, The Netherlands and under cultural conditions which approximate commercial *Cuphea* plant production. During the production of the plants, day temperatures ranged from 18° C. to 30° C., night temperatures ranged from 16° C. to 22° C. and light levels were at a minimum of 135 watts/m$^2$. Plants were pinched one time four weeks after planting and plants were twelve weeks old when the photograph and description were taken. In the following description, color references are made to The Royal Horticultural Society Colour Chart, Fifth Edition, except where general terms of ordinary dictionary significance are used.

Botanical classification: *Cuphea hyssopifolia* 'Docupla 24'.

Parentage:

- *Female, or seed, parent*.—Proprietary selection of *Cuphea hyssopifolia* identified as code number CU-0010, not patented.
- *Male, or pollen, parent*.—Proprietary selection of *Cuphea hyssopifolia* identified as code number CU-0021, not patented.

Propagation:

- *Type*.—By vegetative cuttings.
- *Time to initiate roots, summer*.—About 14 days at temperatures about 22° C. to 30° C.
- *Time to initiate roots, winter*.—About 14 days at temperatures about 20° C. to 22° C.
- *Time to produce a rooted young plant, summer*.—About 21 days at temperatures about 22° C. to 30° C.
- *Time to produce a rooted young plant, winter*.—About 24 days at temperatures about 20° C. to 22° C.
- *Root description*.—Fine, fibrous; typically white to grey in color, actual color of the roots is dependent on substrate composition, water quality, fertilizers, substrate temperature and age of roots.
- *Rooting habit*.—Moderately freely branching; medium density.

Plant description:

- *Plant and growth habit*.—Herbaceous annual; compact and semi-upright growth habit; freely branching habit; moderately vigorous growth habit and moderate growth rate.
- *Plant height*.—About 15 cm.
- *Plant diameter*.—About 35 cm.

Lateral branch description:

- *Quantity*.—About four to five primary lateral branches each with about five to six secondary lateral branches develop on pinched plants.
- *Length*.—About 15 cm to 20 cm.
- *Diameter*.—About 2 mm to 3 mm.
- *Internode length*.—About 2 cm to 3 cm.
- *Aspect*.—Upright to outwardly spreading.
- *Strength*.—Moderately strong.
- *Texture and luster*.—Smooth, glabrous; matte.
- *Color, developing stems*.—Close to 174A.
- *Color, developed stems*.—Close to 165B; if woody, close to 165A.

Leaf description:

- *Arrangement*.—Opposite; simple; sessile.
- *Length*.—About 2.5 cm.
- *Width*.—About 7 mm.
- *Shape*.—Oval.
- *Apex*.—Acute.
- *Base*.—Acute.
- *Margin*.—Entire.
- *Texture and luster, upper surface*.—Smooth, glabrous; glossy.
- *Texture and luster, lower surface*.—Pubescent, soft; matte.
- *Venation pattern*.—Pinnate.
- *Color*.—Developing leaves, upper surface: Close to 139A. Developing leaves, lower surface: Close to 137C. Fully expanded leaves, upper surface: Close to 139A; venation, close to 144C. Fully expanded leaves, lower surface: Close to 137D; venation, close to 144A.

Flower description:

- *Flower arrangement and habit*.—Single tubular stellate flowers with flaring petals; flowers arising from leaf axils; freely flowering habit with about 100 flowers developing per plant during the flowering season; flowers face upright to outwardly; flowers sessile.
- *Fragrance*.—None detected.
- *Natural flowering season*.—Plants flower continuously throughout the summer in The Netherlands; early flowering habit, plants begin flowering about ten to twelve weeks.
- *Flower longevity*.—Individual flowers last about two to three weeks on the plant; flowers not persistent.
- *Flower buds*.—Length: About 5 mm. Diameter: About 1 mm. Shape: Ovoid. Texture and luster: Smooth, glabrous; matte. Color: Close to 144C.
- *Flower diameter*.—About 7 mm to 8 mm.
- *Flower length*.—About 1.1 cm to 1.2 cm.
- *Petals*.—Arrangement: About five to six petals arranged in a single whorl. Length: About 6 mm to 7 mm. Width: About 3 mm. Shape: Oval. Apex: Bluntly acute. Base: Tapering. Margin: Entire; not undulate. Texture and luster, upper and lower surfaces: Smooth, glabrous; matte. Color: When opening and fully opened, upper surface: Close to 71C; venation, close to 71A; color does not change with subsequent development. When opening and fully opened, lower surface: Close to 72D; venation, close to 71C; color does not change with subsequent development.

*Sepals*.—Arrangement: Six sepals fused in a single whorl; calyx, tubular. Length: About 6 mm. Width: About 1 mm. Shape: Ovate. Apex: Acute. Margin, free part: Entire. Texture and luster, upper and lower surfaces: Smooth, glabrous; semi-glossy. Color, upper and lower surfaces: Close to 144A.

*Reproductive organs*.—Stamens: Quantity per flower: About five to six. Anther length: About 1 mm. Anther color: Close to 26A. Pollen amount: Scarce. Pollen color: Close to 5B. Pistils: Quantity per flower: One. Pistil length: About 5 mm. Style length: About 2 mm. Style color: Close to 4A. Stigma diameter: Less than 1 mm. Stigma shape: Rounded. Ovary color: Close to 4A.

*Seeds*.—To date, seed production has not been observed on plants of the new *Cuphea*.

Pathogen and pest resistance: To date, plants of the new *Cuphea* have not been observed to be resistant to pathogens and pests common to *Cuphea* plants.

Garden performance: Plants of the new *Cuphea* have been observed to have good garden performance and tolerate wind, rain and to tolerate temperatures ranging from about 10° C. to 40° C.

It is claimed:

1. A new and distinct *Cuphea* plant named 'Docupla 24' as illustrated and described.

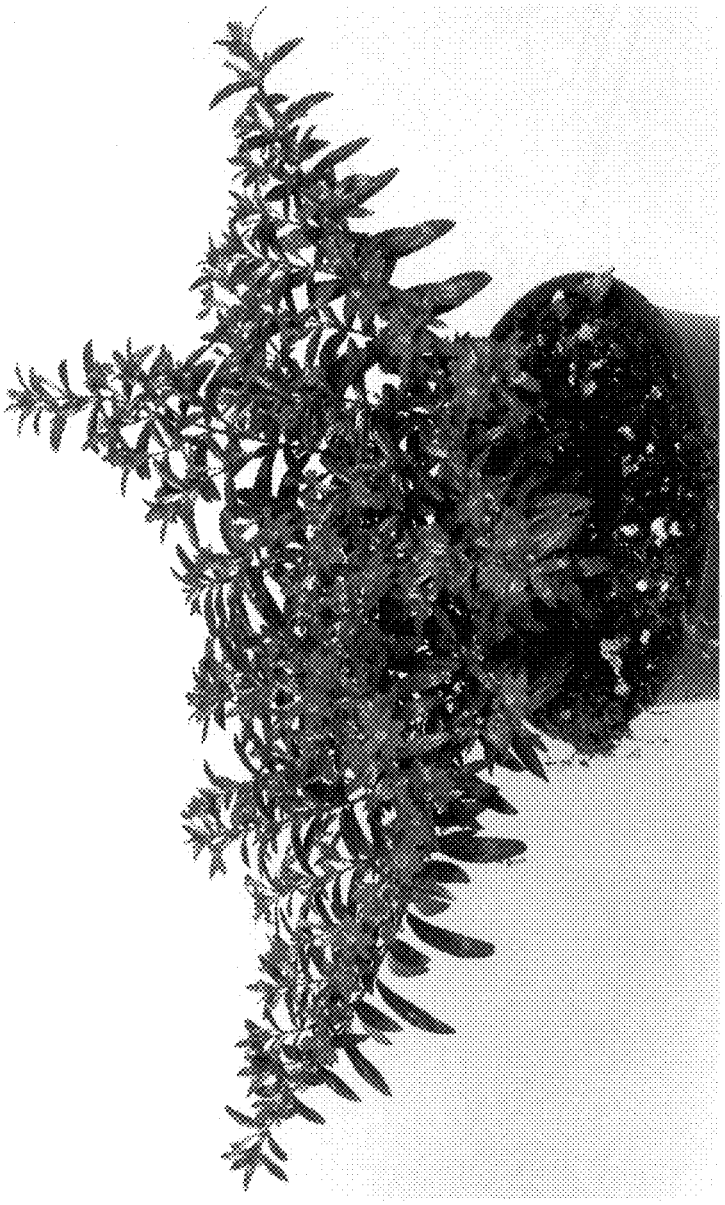

* * * * *